(12) United States Patent
Carinci et al.

(10) Patent No.: US 7,955,850 B2
(45) Date of Patent: Jun. 7, 2011

(54) STEM CELLS OBTAINED FROM PULP OF DECIDUOUS OR PERMANENT TEETH AND OF DENTAL GERM, ABLE TO PRODUCE HUMAN BONE TISSUE

(76) Inventors: Francesco Carinci, Bologna (IT); Riccardo D'Aquino, Naples (IT); Alfredo De Rosa, Naples (IT); Antonio Graziano, Naples (IT); Gregorio Laino, Torre Del Greco (IT); Gianpaolo Papaccio, Naples (IT)

( * ) Notice: Subject to any disclaimer, the term of this patent is extended or adjusted under 35 U.S.C. 154(b) by 567 days.

(21) Appl. No.: 11/658,524

(22) PCT Filed: Jul. 27, 2005

(86) PCT No.: PCT/EP2005/008136
§ 371 (c)(1),
(2), (4) Date: Sep. 15, 2008

(87) PCT Pub. No.: WO2006/010600
PCT Pub. Date: Feb. 2, 2006

(65) Prior Publication Data
US 2009/0035376 A1    Feb. 5, 2009

(30) Foreign Application Priority Data
Jul. 28, 2004    (IT) .............................. NA2004A0043

(51) Int. Cl.
*C12N 5/071* (2010.01)
(52) U.S. Cl. ..................................................... 435/366
(58) Field of Classification Search ................... 435/366
See application file for complete search history.

(56) References Cited

U.S. PATENT DOCUMENTS

| | | | |
|---|---|---|---|
| 5,306,305 A | 4/1994 | Lee | 623/16 |
| 2004/0058442 A1 | 3/2004 | Shi et al. | 435/366 |
| 2007/0274958 A1* | 11/2007 | Shi et al. | 424/93.7 |

OTHER PUBLICATIONS

Shi et al., "Perivascula Niche of Postnatal Mesenchymal Stem Cells in Human Bone Marrow and Dental Pulp", J Bone Min Res 18(4):696-704 (2003).
Gronthos et al., "Postnatal Human Dental Pulp Stem Cells (DPSCs) in vitro and in vivo", Proc Nat Acad Sci US 97(25):13625-13630 (2000).
Tsukamoto et al., "Mineralized Nodula Formation by Cultures of Human Dental Pulp-Derived Fibroblasts", Archs Oral Biol 37(12):1045-1055 (1992).
Laino et al., "An Approchable Human Adult Stem Cell Source for Hard-Tissue Engineering", J Cell Physiol 206:693-701 (2006).
Laino et al., "A New Population of Human Adult Dental Pulp Stem Cells: A Useful Source of Living Autologous Fibrous Bone Tissue (LAB)", J Bone Min Res 20(8):1394-1402 (2005).
Miura et al., "SHED: Stem Cells from Human Exfolidated Deciduous Teeth", Proc Nat Acad Sci US 100(10):5807-5812 (2003).

* cited by examiner

Primary Examiner — Thaian N Ton
(74) Attorney, Agent, or Firm — Porzio, Bromberg & Newman, P.C.

(57) ABSTRACT

In this invention is described a method that foresees the isolation of a new subpopulation of stem cells derived form dental pulp, whose differentiation is osteoblasts lead to the subsequent production and employment of a bone tissue, called LAB (Living Autologous Bone). Specifically, the invention describes: 1) the isolation of stem cells from the pulp of deciduous and permanent teeth and of dental germs, obtained from human subjects; 2) the growth of these cells in vitro, under specific conditions that allow the isolation of a cellular sub-population, which, after differentiation in osteoblasts, is able to produce in vitro an extracellular matrix, identical to that detectable in bone tissue; 3) the use of this selected and differentiated cell population in order to produce autologous bone tissue in vitro, containing vital osteoblasts; 4) the preservation of the LAB under conditions which guarantee cellular vitality; 5) the use of the LAB in donor patients to reconstruct bone tissue, as required in the daily practice in dentistry, maxillo-facial surgery and orthopedics.

1 Claim, No Drawings

STEM CELLS OBTAINED FROM PULP OF DECIDUOUS OR PERMANENT TEETH AND OF DENTAL GERM, ABLE TO PRODUCE HUMAN BONE TISSUE

BACKGROUND OF THE INVENTION

The aesthetic, morphological and functional rehabilitation of the oro-maxillo-facial area has reached high standards in recent decades, due to the progress of all disciplines related to dentistry, such as anesthesiology, microsurgery and pharmacology.

However, bone loss is still the limiting step in order to reach a good rehabilitation. Bone loss can be classified regarding the site (i.e. related to the periodontium, jaws, cranio-maxillo-facial area, etc), the quality, the embryological origin, the mechanical bone properties (related to the strength of cancellous bone; Trisi P. And Rao W. Bone classification: clinical-histomorphometric comparison. Clin. Oral Implants Res. 1999, 10:1-7) and the quantity (that can be defined as the total volume of lost bone).

The lost bone can involve the periodontal area, jaws, cranio-facial skeleton and sites of different part of the body. Several are the causes involved:

1—Deficit of anatomical structures fixing the teeth to jaws. The teeth are fixed in the alveolar bone by means of periodontium, composed of gingiva, cement, periodontal ligament and alveolar bone. Periodontal diseases are many illnesses due to genetic and environmental factors. The clinical sign is an alveolar bone resorption and a loss of teeth attachment. The degree of illness is scored as vertical bone loss and number of alveolar walls involved. As the maximum length of dental root is around 20 mm, the maximum vertical bone loss with teeth still in place cannot be higher (Lindhe J., Parodontologia, Edi-Ermes, Milano, 1991). Periodontal diseases are epidemic. In some geographical areas, more than 10% of the population has periodontal pockets which can be probed more than 5 mm (Orozco A. H. et al., Periodontal treatment needs in a native island community in Columbia. Int. Dent. J. 2004, 54: 73-76). All these patients need a specific therapy to restore the lost alveolar bone.

2—Deficit of bone in the jaws. These deficits have several causes, such as partial or total edentulism (that causes alveolar bone resorption), trauma and tumors. Among tumors, the oral squamous cell carcinoma is the most frequent malignant disease of the mouth with about 30,000 new cases and 8,000 dead patients per year in US (Greenlee R., et al. Cancer statistic. Cancer J. Clin. 2001, 51: 15-36). As regard the facial traumas no national report is still available, but the number of treated patients is very high if one considers that a single center can operate more than 1,000 patients per year (Gassner R. et al. Cranio-maxillo-facial trauma: a 10 year review of 9,543 cases with 21,067 injures. J Craniomaxillofacial Surg. 2003, 31: 51-61).

3—Deficit of Bone in the Craniofacial Area.

There are several causes which determine bone loss. Among them are post-traumatic sequelae, craniofacial resection for tumor removal and malformations. Examples of congenital malformations which require autologous bone grafts are cleft of lip and palate (in this case the autologous bone graft is inserted in the cleft of the alveolar ridge) and the Treacher Collins syndrome (in this case a rib is used to restore the mandible).

4—Deficit of Bone Tissue Outside the Head Region.

There are several causes which determine bone loss. Among them are post-traumatic sequelae, bone resection for tumor removal and malformations. In all these cases the availability of autologous bone to restore the deficit is the limiting step that orthopedics have to overcome in the daily practice.

As reported above, the bone deficit can be classified as minor (as in the periodontal disease) if the bone volume defect is roughly a few millimeters per side and major if the bone loss is bigger.

Today to correct bone defects there are several biomaterials and different surgical techniques. All of them have advantages and disadvantages.

In minor bone defects, there are several medical and surgical procedures to prevent and restore the periodontal disease. However, when the periodontal diseases are severe, we need to restore the bone deficit. This can be reached by using alloplastic or eterolog/xenograft material. Both can produce osteo-induction and/or osteo-conduction. In the same cases the dentist can use membranes which determine a physical separation between epithelium and the underlining bone.

In major bone defects there are three therapeutic possibilities: 1) use alloplastic material (such as mash to reconstruct the mandible or hip prosthesis), 2) use autologous bone graft (such as the iliac crest graft to rebuilt the mandibular arch or free flaps collected from fibula, forearm, iliac crest, etc.), 3) distraction osteogenesis.

In any case, the golden standard is the use of autologous bone. The use of eterologous or xenograft bone can lead to non-self reaction and also to unknown disease transmission, whereas the use of alloplastic materials cannot restore the deficit and moreover is prone to induce infections and foreign-body reactions. Today, there are several limits to an extensive use of autologous bone grafts: 1) the morbility in the donor site (i.e. fibula, forearm, iliac crest, etc) is not always acceptable overall if one considers that sometimes the graft failed; 2) the surgical strategy has relevant costs with regards to instruments and equipe training; 3) the collection of the graft from the donor site enlarges the operation time; 4) it is not possible to collect a high amount of bone from the donor site since it can cause sequelae in it.

Taking into account what above reported, one can conclude that: 1) the bone deficit is the limiting step in the dental, maxillo-facial and orthopedic reconstruction; 2) the autologous bone is the gold standard; 3) to collect autologous bone from a different site of the same patient leads to additional risks for the patient itself, requiring a specific equipe training and has biological and economic costs.

A potential solution to these adverse factors is the use of an autologous bone produced in vitro by using specific cytotypes. From this point of view, the use of stem cells (that are able to differentiate in osteoblasts producing bone in vitro) can be a good strategy.

Stem cells are cells characterized by: 1) self-renewal (i.e. no limit to the potential number of cell division); 2) commitment and differentiation to different cell lines. In literature it has been reported the identification of stem cells derived from bone marrow and able to differentiate in osteoblasts (Kuznetsov S. A., et al. Single-colony derived strains of human marrow fibroblasts from bone after transplantation in vivo. J. Bone Min. Res. 1997; 12, 1335-47; Pittenger M. F., et al. Multilineage potential of adult human mesenchymal stem cells. Science 1999, 284, 143-147), but it is not described the capacity of these cells (named Bone Marrow Stromal Stem Cells—BMSSC) of producing bone in a three-dimensional structure in vitro. More recently, the isolation and characterization of stem cells, derived from human dental pulp has been described. (Gronthos S. et al., PNAS 2000, 97, 13625-13630; Gronthos S. et al., JDR 2002, 81, 531-535; Batouli S. et al., JDR 2003, 82, 976-981; US n. 20040058442 di Shi et al.). Specifically, the Dental Pulp Stem Cell (DPSC) line is a precursor of osteoblasts and is characterized by: 1) the presence of specific dentin sialoprotein; 2) the absence of bone production in vitro; 3) the production of dentin-like structures in vivo, when cells were transplanted in immuno-deficient mice.

Miura M et al. (PNAS 2003; 100, 5807-5812) describe an additional class of stem cells obtained from deciduous dental pulp, called Stem Cells from Human Exfoliated Deciduous teeth (SHED). SHED cells can differentiate in osteoblasts in vitro but they need the addition of BMP-4 to the medium. Moreover SHED cells do not differentiate in osteoblasts when transplanted in immuno-deficient mice. Both SHED and DPSC cells are unable to produce bone tissue in vitro.

In addition both SHED and DPSC need a ceramic vector in order to be transplanted in the animal to obtain a three-dimensional tissue.

Additional patents, related to the state of the art of the present invention, are the US n. 20020119180 (by Yelic et al.) and the US n. 20030068305 (by Sramek et al.). The US n. 20020119180 describes a method to produce dental germ in an animal model. These dental germs can be potentially inserted in human gum to replace lost teeth. The US n. 20030068305 describes a method and a specific tool to collect the dental pulp.

SUMMARY OF THE INVENTION

The invention describes:
1) a method for the isolation of two stem cell lines of mesenchymal and not hematopoietic origin, derived from human dental pulp. These cell lines when derived from dental pulp of permanent teeth or dental germs are called Mesenchymal Bone Producing cells derived from Dental Pulp Stem Cells (MBP-DPSC) and, when derived from pulp of deciduous teeth are called Mesenchymal Bone Producing cells derived from Stem cell of Human Exfoliated Deciduous teeth (MBP-SHED). They can be obtained by using a cytofluorimeter with sorter and specific markers which selected stem antigens;
2) the culture, expansion and differentiation of both stem lines in osteoblasts able to produce bone. This new kind of vital biological material is called Living Autologous Bone (LAB). It is a woven non lamellar bone containing vital osteoblasts derived from MBP-DPSC and MBP-SHED. These cells belong to the pulp of human deciduous and permanent teeth and dental germs. Both MBPs are able to differentiate in osteoblasts without addition of any osteogenic drug in the medium, and the derived osteoblasts produce bone in vitro and in vivo;
3) a method for clinical application of the LAB in the dental, maxillo-facial and orthopedic practice;
4) a method for extensive production of LAB.

DESCRIPTION OF THE INVENTION

The present invention concerns a biological, vital material that can be used for autologous bone graft, and a method for its production from stem cells, derived from the pulp of human deciduous and permanent teeth and of dental germs, able to differentiate in osteoblasts, producing in vitro a woven bone. This vital tissue can be grafted as an autologous material in the donor patient for bone defect repair. Specifically, the invention describes a method for:
1) the isolation of stem cells, derived from human pulp of deciduous and permanent teeth and of dental germs, respectively called MBP-SHEDs and MBP-DPSCs; 2) their expansion (i.e. clone number increase); 3) their differentiation in osteoblasts; 4) the production in vitro of a woven bone tissue produced by these osteoblasts, which is called living autologous bone (LAB); 5) the storage of the LAB under specific conditions which guarantee a high cellular vitality; 6) the transplant of the LAB in the donor patient in order to restore the bone deficit.

The present invention shows the following advantages with respect to prior art, that uses osteoblasts derived from bone marrow stem cells (Kuznetsov S A et al., Single colony derived strains of human marrow stromal fibroblasts from bone after transplantation in vivo. J. Bone Min. Res. 1997, 12, 1335-1347; Pittenger M. F. et al., Multilineage potential of adult human mesenchymal stem cells. Science, 1999, 284, 143-147): 1) reduced invasiveness, in fact it is possible to avoid teeth extraction by performing a pulpectomy; 2) high safety, because the sample collection is performed on a tooth respect to the previously used stern or iliac crest marrow; 3) primary cultures characterized by a high number of colonies, because the samples do not have hematopoietic cells; 4) a three-dimensional organization of the LAB without the addition of any osteogenic drug or scaffold, this cannot be obtained by using osteoblasts derived from marrow stem cells.

In addition, the present invention, shows some other advantages with respect to the prior art related to the already known DPSC cells (Gronthos S. et al., PNAS 2000, 97, 13625-13630; Gronthos S. et al., JDR 2002, 81, 531-535; Batouli S. et al., JDR 2003, 82, 976-981; US n. 20040058442 by Shi et al.) and to SHED cells (Miura M et al., PNAS 2003, 100, 5807-5812) isolated from human dental pulp. The MBP-DPSC, described in the present invention derive from the mesechyme and not from haematologic tissue (as was the case for the previously reported DPSC). Moreover, the MBP-DPSC differentiate in osteoblasts able to produce bone in vitro whereas the DPSC do not. The DPSC can produce bone-like structures only when transplanted in immuno-deficient mice.

The MBP-SHED cell is different from the SHED, because these: 1) need the addition of BMP-4 to the medium, to differentiate in osteoblasts in vitro; 2) are not able to produce bone-like tissue in vitro; 3) if transplanted in immuno-deficient mice, are not able to differentiate in osteoblasts, but induce the formation of a dentin-like tissue.

An additional difference between the present invention and the prior art is related to the method employed for the isolation of stem cells from human pulp of deciduous and permanent teeth and of dental germs (i.e. the FAC sorter use).

In addition DPSC and SHED cells need the use of a ceramic vector to be transplanted in the animal model, whereas the LAB can be transplanted alone.

In a similar way there are many differences between the present invention and the US n. 20020119180 by Yelic et al., and the US Patent n. 20030068305 by Sramek et al. The US n. 20020119180 describes a method to produce dental germ in an animal model. These dental germs can be potentially transplantable in human gum to replace lost teeth. The US n. 20030068305 describes a method and a specific tool to collect the dental pulp and isolate supposed stem cells, which are completely different from those described in the present invention.

Description of the Method to Obtain MBP-Shed and MBP-DPSC from Human Pulp of Deciduous and Permanent Teeth and of Dental Germs.

Stem cells isolated from human dental pulp derive from mesenchymal cells produced by neural crests.

In order to isolate stem cells from human dental pulp it is necessary that the teeth are healthy and without any communication between pulp and oral cavity. The patient should have a professional oral hygiene a week before the tooth extraction (or pulpectomy) and start an antimicrobial prophylaxis with mouth rinses of 0.12% chlorhexidine solution twice a day. In regards to the teeth preparation just before the sampling, there are different methods. The crown is covered with a 0.2% chlorhexidine gel for some minutes. Then the tooth is gently removed with sterile forceps and, by maintaining the tooth with the forceps, the pulp is removed by using a Gracey curette. Immediately after, the pulp is placed in the digestive solution (see below).

If a permanent tooth has to be used there are two methods. The first method is a tooth extraction. The crown is covered with a 0.2% chlorhexidine gel for some minutes. Then the tooth is gently removed with sterile forceps, placed on a sterile drape, washed with 0.12% chlorhexidine solution, and cut in two with a chisel or with a drill under irrigation. The pulp is collected by using a Gracey curette. Immediately after, the pulp is placed in the digestion solution (see below).

The second method is the pulpectomy, leaving the tooth in place. For the procedure one should not use the drill to expose the pulp chamber, because it could damage the pulp. The pulp is collected by using a Gracey curette. Then, the pulp is placed in the digestion solution (see below).

As regard the collection of the pulp from the dental germs the method is similar to that described in case of permanent teeth extraction.

In any case, the dental pulp is placed in a digestive solution containing: 100 U/ml penicillin, 100 µg/ml streptomycin, 500 µg/ml claritromycin in 4 ml PBS 0.1M pH 7.4, added of 3 mg/ml type I collagenase, 4 mg/ml dispase. The solution volume is dependent upon the volume of the pulp to be digested and ranges from 2 to 4 ml in the case of deciduous teeth and from 2 to 5 ml in the case of permanent teeth or dental germs. The pulp is maintained in the digestion solution for 1 h at 37° C., with a gentle shaking, in order to facilitate tissue dissociation. Once digested, the solution is immersed in a 10-fold volume of $\alpha$-MEM culture medium, added with 20% FBS, 100 µM 2P-ascorbic acid, 2 mM L-glutamine, 100 U/ml penicillin, 100 µg/ml streptomycin (Invitrogen, Milan, Italy). Cell suspension is then centrifuged (10 min at 140 g), the bottom of the tube is resuspended in 12 ml of the same culture medium, filtered onto 70 µm Falcon strainers (Becton & Dickinson, Sunnyvale, Calif., USA). After filtration, cells are placed in 25 $cm^2$ flasks. Flasks are incubated at 37° C. in a 5% $CO_2$ and the medium changed twice a week.

Microscopic observations show that, by day one of culture, two cytotypes can be observed: a) small and rounded cells, forming aggregates of 10 to 30 cells (small colonies); b) spider shape, elongated and adherent cells, forming aggregates of 30 to 80 cells (larger colonies). Up to day 5 of culture, cells do not show a significant proliferation, and the necrotic material present is lost during the medium changes. After 10-15 days of culture, when up to 40 clones were observed in each pulp, the following operations are performed: the medium is removed within the flask; cells are washed twice with sterile PBS 0.1M; cells are detached from the flask. with 0.3 ml of 0.1M trypsin for 1 min at 37° C.; cells are suspended in 3 ml of the culture medium (previously described); 1.5 ml of this suspension are transferred in a second flask; in both flasks is added culture medium up to the final volume of 6 ml. This last step is important to stimulate cell proliferation.

At day 20-21, when the total number of the cells is sufficient to perform the FACsorting, cells are pelleted (10 min at 140 g), washed in 0.1% BSA in PBS 0.1M at 4° C. and incubated for 10 min at 4° C. for antibody challenging in a solution containing 1 µl of the antibody mother solution and 9 µl of 0.1% BSA in PBS. The antibody mother solution is made of 200 µg of the antibody in 1 ml PBS 0.1M. After incubation, cells are washed with BSA 0.1% in PBS, to remove the antibodies which do not react or not specifically react, and are analyzed for the positivity to the following monoclonal antibodies (FITC, PE and Cychrome labeled) against: c-kit, CD34, STRO-1, CD45 (Santa Cruz). Cells showed an 11% positivity for c-Kit, 8% positivity for CD34 and 30% positivity for STRO-1. In particular, cells that were positive for c-kit were also positive for CD34 and STRO-1, while they were always negative for CD45. Therefore we can stress a non haematic origin of these cells. We have collected only these c-kit CD34 and STRO-1 positive cells, to obtain an osteogenic differentiation. c-kit is a membrane tyrosin-kinase which selectively recognize the stem cells factor (SCF). This is performed to isolate stem cells from the pulp of deciduous and permanent teeth and of dental germs, with the only difference that stem cells obtained from deciduous teeth and dental germs are obtained constantly and in a rather high number, while those obtained from permanent teeth are of lower number, although sufficient, but not constantly. These cells, named MBP-SHED and MBP-DPSC, are a stem cell subpopulation of deciduous (SHED) and permanent (DPSC) teeth, both erupted or germs. MBP-SHED and MBP-DPSC differentiate, under specific culture conditions, in osteogenic progenitors, then in osteoblasts, as follows: STEM CELLS (identified as c-kit, CD34 and STRO-1 positive cells)→PROGENITOR/PRECURSOR CELLS (identified by RUNX-2 positivity)→TERMINALLY DIFFERENTIATED CELLS (identified by osteocalcin and CD44 positivity). This differentiation is described below.

The c-kit, CD34 and STRO-1 positive stem cells are plated. They proliferate in each flask. By day 30 from isolation, cells start to produce an extra cellular organic matrix which, by day 40, within the flasks, produces a woven bone (LAB), in which the same cells responsible of its formation are observed.

LAB formation is characterized by these steps: 1) initially groups of cells form a rounded central area, in which they secrete inorganic crystals, collagenic fibres and glycoproteins; 2) then this structure acquires a 3D organization due to new matrix apposition; 3) by day 40 the matrix becomes a 3D mineralized tissue, which is a woven bone (non lamellar bone); 4) by day 50, within the flasks, small cubes of bone tissue are observable, whose dimensions are dependent from the medium height. This method allows to obtain small cubes of woven bone, having 1 cm of thickness and a volume up to 1 $cm^3$, which are suitable for surgical implants, also because they are rich of living osteoblasts, in synthetic activity, able of bone deposition.

When cells become confluent, they do not further proliferate but, if some of them are taken away and put in another flask, they re-start to proliferate and produce LAB. Therefore, the developed system allows to realize a bioreactor able to produce LAB, without limitations. Then, after cell differentiation, by day 35 from their isolation, cell characterization is performed, by using monoclonal antibodies: HLA-1, CD14, CD44, CD45, CD54, SSEA-1, RUNX-2, CD34, OSTEOCALCINA (OC) and flk1. Cells obtained with this invention show a 100% positivity for HLA-1 and CD44, a 70% positivity for RUNX-2 and 30% positivity for OC, CD54 and flk-1, while they are completely negative for the other antibodies which are used. RUNX-2 is a transcription factor, which identifies a pre-osteoblastic cytotype, while OC identifies osteoblasts. Stem cells, which during the differentiation process express flk-1 (VEGF receptor, or vasculo-endothelial growth factor), are responsible for angiogenesis, which may happen within the central part of the LAB. In fact, cells which are within the neoformed LAB do not degenerate and indefinitely produce woven bone, which can be used for autologous transplants. The LAB maintains its characteristics and vitality after storage at +4° C. for many days. Moreover LAB may be cryopreserved and stored at temperatures <0° C. for a long time, maintaining its abilities of osteo-generation, by using conventional cryo-conservation techniques for cells and tissues.

In summary, the procedure to obtain LAB is the following: 1) extraction, in sterility, of pulp from deciduous and permanent teeth or dental germs, digestion and culture; 2) trypsinization and amplification of primary cultures; 3) FAC-sorting and re-starting of culture; 4) cell differentiation with tissue formation and their use to increase tissue formation through its dissemination in several flasks with the use of new culture medium.

In the following Table the timing of the whole process, which allows to continuously obtain LAB production (depending on patient treatment) is reported:

| Phase | Day |
| --- | --- |
| Tooth extraction | 0 |
| Pulp collection from deciduous and permanent tooth or dental germ | 0 |
| Pulp digestion | 0 |
| Culture starting point | 0 |
| Cell proliferation | 1-15(21) |
| Sorting | 15-21 |
| Osteogenic differentiation | 16-22 a 35 |
| Characterization (RUNX-2 and OC) | 35 |
| LAB production | 40-ad libitum |
| LAB transplantation | After 50 |
| Bone defect healing | Within 60 days from transplantation |

LAB Characterization.

The obtained mineralized living autologous woven bone in vitro (LAB) shows characteristics which are similar to those of a human bone during mineralization; in fact, images are perfectly super imposable to those of human bone in direct or membranous ossification.

The characteristics of LAB production: 1) cells with characteristic and specific stem expressions are obtained by means of the claimed procedure from the pulp of human deciduous and permanent teeth, or dental germs. In the case of permanent teeth stem cells have been obtained also from individuals of not young age; 2) stem cells, by means of appropriate treatments, differentiate in an osteogenic cytotype, that begins to produce a mineralized matrix and, subsequently, an autologous mineralized living bone, showing the same characteristics of the human bone during ossification; 3) histological, histochemical, (Alizarin Red S, ALP, Schmorl, H&E), immunofluorescence (positivity to calcein and antibodies directed against osteonectin, osteopontin, fibronectin, collagen type III and bone phosphatase alkaline), and X ray diffraction observations clearly demonstrate the similarity between the LAB and human bone during mineralization; 4) the cells present in the LAB grow and produce bone without cytological modifications; 5) the vital bone obtained in vitro (LAB) can easily be transferred in other flasks, where it continues to grow in the culture medium; 6) after trypsinization bone cells obtained are able to produce bone in a secondary cultivation flask; 7) the LAB and cells in it remain vital if maintained to +4° C. for 24-36 hours; 8) the LAB and cells in it can be cryopreserved at temperatures <80° C. for years, using the conventional techniques for the cryoconservation of cellular material.

In conclusion, the present invention differs from the prior art; in particular from that of Miura and Gronthos, for the following: 1) the technique of pulp extraction from both permanent and deciduous teeth is different; 2) the use of the pulp of dental germs to isolate stem cells; 3) the selection of the cellular types based on the FACsorter; 4) the isolated stem population is c-kit, CD34, and STRO-1 positive, but always and constantly negative for CD45, that indicates that cells are not haematopoietic, differently from how reported by Gronthos and Miura; 5) the percentage of positivity and the number of obtainable cells are more elevated respect to the prior art; 6) the isolated cells produce in vitro living autologous mineralized bone (LAB), while the works of Miura and Gronthos do not describe this ability, but only the fact that the isolated cells, injected in immunodepressed rats stimulate the woven production of a dentin-like material; 7) the cells isolated from Gronthos and Miura are "a heterogeneous" population, while the methodology described in the present invention concurs the selection of a homogenous cellular population; 8) contrarily with that reported by Gronthos the methods concur to isolate stem cells in a sufficient number, also in the case of permanent teeth of individuals more than 32 years old; 9) the LAB grows without limits, if not those due to the surface and culture medium available; 10) the cells described in the invention are highly stable and produce bone, that is super imposable to that seen in humans during mineralization and not merely crystals, like described from Gronthos and Miura; 11) the cells of the invention are osteoblasts and not odontoblast-like cells, as reported by Gronthos and Miura. Transmission electron microscopy of MBP-SHED and MBP-DPSC shows a conspicuous vesicular traffic, from and towards the cell and numerous ultra structural peculiarities have been observed at the level of the nuclear structures. Frequent it is, in fact, the presence of plurinucleated cells, in some cases the nuclei turn out irregular with more than a nucleolus. A common characteristic of all the nuclei is the presence of a filament or of an extension perhaps to a lobe nuclear. These characteristics are typical of undifferentiated stem cells. TEM analysis of differentiated osteoblasts and of the woven bone obtained has shown that the cells possess a cytoplasm rich of vesicles, typical of human osteoblasts, a particularly abundant RER, a nucleus with a nucleolus, all signs of an active proteic synthesis. The extracellular matrix appears rich of fibers and proteoglycans, and of esoytotic vesicles. These features are typical of differentiated cells secreting matrix, similar to the characteristics observed in the human bone in formation.

To better address the shape of the neoformed woven bone in 3D, cells are grown on a reabsorbable polylactic-coglycolic acid (85:15 p/p) polymer. This polymer matrix has been taken in examination for its facility of manipulation and for the resorption time, that allows the morphologic address of the woven bone, but at the same time does not inhibit the growth. This polymer, once modelled, with a CAD/CAM technique, shows on the surface pores with a diameter of 100-140 $\mu$m, where the cells penetrate, and pores of approximately 15 $\mu$m of diameter, which MBP-SHED or MBP-DPSC join perfectly, with a complete adhesion between cells and polymer.

The behaviour of the MBP-SHED or MBP-DPSC is analogous when these cells are grown on titanium etched surfaces.

The effectiveness of the interaction cell-polymer or cell-titanium has been demonstrated with histological, histochemical (Alizarin Red S, ALP, Schmorl, H&E), immunofluorescence (positivity to the calcein, to antibodies directed against osteonectin, osteopontin, fibronectin, collagen type III and alkaline phosphatase bone), X ray diffraction, and microscopy (confocal, TEM and SEM) studies.

A specific description of the present invention is given in the following examples.

Example 1

Production of LAB from Deciduous Teeth a) Surgical Phase

1) Selection of the patient—All subjects were healthy for systemic and oral diseases. The LAB production has been obtained from deciduous teeth of three patients of male sex 2, 6 and 8 years old.

2) Preparation of the patient to the study—The three patients, the week before the extraction, have been subjected to a professional hygiene and treatment with 0.12% chlorhexidine. As far as the treatment of the tooth at the moment of the withdrawal, the clinical crown has been covered with a 0.2% chlorhexidine gel, for some minutes before provoking exfoliation.

3) Pulp extraction procedures—For the extraction of the deciduous tooth a delicate avulsion by using a sterile clamp for dental extraction has been done. Maintaining the tooth between the branches of the clamp, ex-oris, the tooth has been cleansed with one solution of chlorhexidine 0.12%, before provoking exfoliation. Then the pulp has been exposed and the pulp extracted using a Gracey curette. The pulp was then placed in a test-tube with 5 ml PBS digestive solution containing 3 mg/ml Type I collagenase, 4 mg/ml dispase, 100 U/ml penicillin, 100 mg/ml streptomycin, 500 mg/ml claritromycin. The pulp was immersed in the solution and maintained for 1 hour at 37° C., under moderate agitation in order to facilitate the dissociation of the pulp. At the end, the digested mixture has been 10 fold diluted with culture medium (α-MEM type, added of 20% bovine fetal serum, 100 mM ascorbic acid 2P, 2 mM L-glutamine, 100 U/L penicillin, 100 mg/ml streptomycin) and centrifuged for 10 min at 140 g. After the centrifugation, from the bottom of the test-tube 12 ml of the suspension were taken and filtered using 70μ Falcon strainer.

b) Laboratory Phase

1) Preparation of primary cultures—The filtered solution was placed in a flask and put in an incubator (37° C. and 5% C02), carrying out changes of the medium twice a week.

2) Expansion of the cultures—Cells were made to proliferate in the flask, leaving them in culture at least for 15 days.

3) Characterization of the various clones—When the number of the cells was thought to be sufficient (approximately 500,000 cells), cells have been selected through FACsorting, using markers for stem cells including CD34, STRO-1 and c-Kit.

4) Isolation of the specific stock called MBP-SHED—From the culture, positive cells to CD34, STRO-1 and c Kit were selected and used for the subsequent expansion and differentiation.

5) Expansion of specific MBP-SHED clones in vitro. The cells made to grow in the medium of culture, previously described at the point a3).

6) Production of the LAB—After several passages, a living autologous woven bone colonized from osteoblasts (LAB) has been obtained. This phase lasted approximately 40 days, for having a complete differentiation of the stem cells to osteoblasts.

7) Expansion of the LAB—Starting with 100,000 MBP-SHED the LAB production requires 10 to 15 passages in a 25 ml flask each with 6 ml of medium; such passages were carried out in approximately 8 weeks, obtaining about 2 cm$^3$ of bone.

8) Use of the LAB for histological studies.

Example 2

Production of LAB from Permanent Teeth a) Surgical Phase

1) Selection of the patient—The selection of the patients was carried out considering clinical parameters and pathological condition. All subjects were healthy for systemic and oral diseases. LAB production was performed from permanent teeth of five male patients 30, 32, 34, 35 and 37 years old. In this phase dental donor sites were identified: all third molars, two upper and three lower.

2) Preparation of the patient—A week before tooth extraction, the patients were subjected to a professional dental hygiene and to rinsing with chlorhexidine 0.12% solution twice a day for all the week that proceeded the extraction.

3) Pulp extraction procedures—After local anaesthesia, tooth extraction was performed with lever and/or clamp. For the lowers this procedure was preceded by a surgical access through execution of a mucoperiosteum flap. Keeping the extirpated element between the branches of the clamp, extra oris, the dental element has been placed on a sterile surgical cloth and cleaned with a 0.12% chlorhexidine solution. Therefore, the pulp chamber exposed through the separation between crown and anatomical root, using cutter sterile mounted on a surgical micro motor, with sterile water irrigation. The pulp is collected using a Gracey curette and/or endodontic tools, like files, and immersed in 5 ml of digestive solution (in 4 ml PBS) 1M containing 100 U/ml penicillin, 100 μg/ml streptomycin, 500 μg/ml claritromycin, 3 mg/ml type I collagenase, 4 mg/ml dispase for 1 h at 37° C. The pulp during digestion was kept in slow agitation in order to facilitate the dissociation of the tissue. At the end of digestion was added culture medium (α-MEM culture medium, added with 20% FCS, 100 μM 2P-ascorbic acid, 2 mM L-glutamine, 100 U/ml penicillin, 100 μg/ml streptomycin) to a volume of 50 ml and samples centrifuged for 10 min to 140 g. Then, 12 ml of solution were collected from the bottom of the tube and filtered onto a 70μ strainer.

b) Laboratory Phase.

1) Preparation of primary cell culture—Filtered solution was placed in a flask and incubated at 37° C. and 5% $CO_2$;

2) Proliferation of cell culture—Culture medium was changed twice a week for at least 15 days;

3) Cell characterization—When the number of the cells was about 500.000, FACsorting was performed using stem markers CD 34, Stro-1 and c Kit.

4) Isolation of MBP-DPSC—After FAC Sorting positive cells were collected and cultured.

5) Proliferation of MBP-DPSC in vitro—Cells were cultured with previous culture medium.

6) LAB production—Several passages were performed from stem cells to differentiated osteoblasts LAB producing. This experimental phase took about 40 days.

7) LAB expansion—After 10-15 passages of differentiated osteoblasts, to obtain enough cells, LAB was obtained plating samples of 100,000 cells in 25 ml flasks with 6 ml of culture medium. This phase was carried out in approximately 8 weeks, until obtaining a bone chip each flask. Bone chips reach the volume of about 1 cm$^3$ volume.

8) Collection of the LAB from the flask for histological analyses.

Example 3

Production of LAB from Dental Germs a) Surgical Phase.

1) Selection of the patient—The selection of the patients was carried out considering clinical parameters and pathological condition. All subjects were healthy for systemic and oral diseases. LAB production was performed from dental germs of eight male and female patients 15, 16, 17, 17, 18, 20, 20, and 22 years old. In this phase dental donor sites (all dental germ not still erupted) were identified: all third molars, three upper and five lower.

2) Preparation of the patient—A week before teeth extraction, the patients were subjected to a professional dental hygiene and to rinsing with chlorhexidine 0.12% solution twice a day for all the week that proceeded the extraction.

3) Pulp extraction procedures—After local anaesthesia, tooth extraction was performed with lever and/or clamp. For the lowers this procedure was preceded by a surgical access through execution of a mucoperiosteum flap. Keeping the extirpated element between the branches of the clamp, extra oris, the dental element has been placed on a sterile surgical cloth and cleaned with a 0.12% chlorhexidine solution. Therefore, the pulp chamber was exposed through the separation between crown and anatomical root, using cutter sterile mounted on a surgical micro motor, with sterile water irrigation. The pulp is collected using a Gracey curette and/or endodontic tools, like files, and immersed in 5 ml of digestive solution (containing in 4 ml PBS 1M:100 U/ml, 100 µg/ml streptomycin, 500 µg/ml claritromycin 4 ml PBS 1M, added of 3 mg/ml type I collagenase, 4 mg/ml dispase) for 1 h at 37° C. The pulp during digestion was kept in slow agitation in order to facilitate the dissociation of the tissue. At the end of digestion culture medium was added ($\alpha$-MEM culture medium, added with 20% FCS, 100 µM 2P-ascorbic acid, 2 mM L-glutamine, 100 U/ml penicillin, 100 µg/ml streptomycin) to a volume of 50 ml and samples centrifuged for 10 min to 140 g. Then, 12 ml of solution were collected from the bottom of the tube and filtered onto a 70 micron strainer.

b) Experimental Phase.

1) Preparation of primary cell culture—Filtered solution was placed in a flask and incubated at 37° C. and 5% C02;

2) Proliferation of cell culture—Culture medium was changed twice a week for at least 15 days.

3) Cell characterization—When the number of the cells was about 500,000, FACsorting was performed using stem markers CD34, STRO-1 and c-Kit.

4) Isolation of MBP-DPSC—After FACsorting positive cells were collected and cultured.

5) Proliferation of MBP-DPSC in vitro—Cells were cultured with previous culture medium:

6) LAB production—Several passages were performed from stem cells to differentiated osteoblasts LAB producing. This experimental phase requires roughly 40 days.

7) LAB expansion—After 10-15 passages of differentiated osteoblasts, to obtain enough cells, LAB was obtained plating samples of 100,000 cells in 25 ml flasks with 6 ml of culture medium. This phase was carried out in approximately 8 weeks until obtaining a bone chip each flask. Bone chips reached a volume of about 1 cm$^3$.

8) Collection of the LAB from the flask for histological analyses.

Example 4

LAB Characterization

LAB samples obtained in Examples 1-3 were subjected to following analyses:

1) LAB number evaluation—Living autologous bone formation has been evaluated. The number of calcified nodules per flask was counted and a comparison between young and old subjects was performed. Data were given as means±SD.

2) Histology, histochemistry and immunofluorescence—Differentiated cells and calcified matrix were removed from flasks using a solution of 50/50 trypsin 1M and 0.5% EDTA, then fixed in 4% formaldehyde in 0.1 M PBS for 48 h at 4° C. pH 7.4, washed in 0.1M PBS pH 7.4 at 4° C., then dehydrated, embedded in paraffin and sectioned (5 µm thick). Slides were stained with haematoxylin-eosin, alizarin red and Schmorl silver nitrate.

For histochemistry and immunofluorescence, cells were washed in 0.1M PBS and fixed in 4% formaldehyde in 0.1 M PBS, with 0.2% Triton X100 for 30 min at 4° C., then washed twice in 0.1% BSA in 0.1M PBS at room temperature for 10 min each. Cells were covered using alkaline phosphatase (ALP) standard solution, incubated in dark for 8 h. ALP activity was performed using 100,000 cell samples, detached by means of PBS/EDTA 0.02% and centrifuged for 10 min at 140 g. The pellet was incubated with 1 ml of BMPurple solution (Roche, Segrate, Milan, Italy) for 8 hours in dark. Supernatant was read in a spectrophotometer at 615 nm. As control, c-kit$^-$/CD34$^-$ cells were used. The values were expressed as ratio between sample and BMPurple stock solution. BMPurple solvent was used as blank.

For immunofluorescence, cells were washed twice in 0.1M PBS at room temperature for 10 min, fixed in 4% formaldehyde in 0.1 M PBS for 48 b at 4° C. pH 7.4, washed in 0.1M PBS pH 7.4 at 4° C., then incubated overnight at 4° C. with antibodies. LAB samples were embedded in TBS (tissue freezing medium, Triangle Biomedical Sciences, Durham, N.C., USA) and cryosectioned (Cryostat 1720 Digital MGW Lauda, Leika, Germany), fixed in 100% ethanol for 30 min at 4° C., washed in PBS 0.1M, then left for 60 min in PBS/milk 6% and incubated with antibodies at 4° C. overnight.

Antibodies for cells or LAB were the following: osteonectin, fibronectin (Novo Castra, Newcastle, UK), BSP (Bone Sialoprotein) (BIODESIGN International, USA), BAP (bone alkaline phosphatase) (US Biological, USA), all mouse anti-human; osteocalcin and collagen III (Santa Cruz, Calif., USA) were goat anti-human. The secondary antibodies were goat anti-mouse (FITC) and mouse anti goat (PE conjugated) (Santa Cruz, Calif., USA). Cells and LAB were observed under the fluorescence microscope (Fluorescence microscope Axiovert 100, Zeiss, Germany).

3) Reverse transcriptase polymerase chain reaction analysis—Total RNA was extracted from about 1,000,000 cells at different times (day 22 for non differentiated cells and day 40 and day 60 for differentiated cells), by homogenization in TRI Reagent (SIGMA, Milan, Italy), following the manufacturer's instructions and stored at −70° C. until the assays. cDNA synthesis was carried out from total RNA using Superscript II reverse transcriptase (Invitrogen Celbio Italy, San Giuliano Milanese, Milan, Italy), using oligo (dT)$_{12-18}$ and Moloney murine leukemia virus reverse transcriptase (10 U/µl) in 20 µl at 42° C. for 50 min.

PCR analyses were made in triplicates using a TC-312 thermal cycler (Techne, Burlington, N.J., USA), in which samples underwent to a 2 min denaturing step to 94° C., followed by 35 cycles of 94° C. for 30 s, 54° C. for 45 s, 72°

C. for 1 min and a final extension step at 72° C. for 4 min. The PCR mixture contained 0.2 mM of each dNTP, 1.5 mM $MgCl_2$, 0.2 µM of each primer. The primer sequences were: forward RUNX-2 5'-CAC TCA CTA CCA CAC CTA CC-3'; reverse RUNX-2 5'-TTC CAT CAG CGT CAA CAC C-3'; forward β-actin 5'-TGT GAT GGT GGG AAT GGG TCA G-3'; reverse β-actin 5'-TTT GAT GTC ACG CAC GAT TTC C-3'. The amplification products were separated on 2% agarose gel in Tris acetate EDTA (TAE) buffer. PCRs were performed on RT-negative samples to exclude DNA contamination.

By immunofluorescence, LAB was largely positive to markers for fibrous bone tissue such as fibronectin, collagen I and III, BSP (Bone Sialoprotein) and BAP, osteonectin and osteocalcin: in particular, osteoblasts forming the monolayer surrounding the new formed trabeculae of the LAB were intensely positive for osteocalcin, further indicating that these cells were osteoblasts involved in the ossification process. Results showed that sorted and cultured cells, by day 50 albeit not more positive for stem cell markers, were positive for CD44 (100%), for RUNX-2 (68.65%±2.0), and osteocalcin (28.45%±1.7). RT-PCR analysis for RUNX-2 has demonstrated that the mRNA transcripts of this transcription factor were present in differentiated cells at days 40 and 60 but not in sorted and not yet differentiated cells, at day 22.

Example 5

Formation and Development of the LAB on Scaffold Polymer

Cell samples according to examples 1-3, are placed to the inside of a cylindrical container in which a preformed fragment of 85:15 p/p lactic-coglycolic acid polymer is introduced (in clinical practice the chosen shape will trace the skeletal bone defect to correct the subject donor). The three-dimensional cell colonization of the preformed scaffold is obtained using a rotating incubator (Roller Apparatus Weaton) at a speed of 6 turns/minute. After approximately 7 days the cells colonize the entire scaffold, originating a 3D LAB of the same polymer shape, digesting, in part the polymer matrix. At this point, the complex scaffold+ cells can be transplanted in vivo, where it will restore the anatomo-functional continuity of the skeletal body. In vivo the process of polymer matrix biodegradation will continue, gradually replaced from the new formed bone matrix secreted from the colonizing cells. The polymer matrix disappears and, in the centre of the system, vital bone that gradually goes encounter to remodelling and become indistinguishable from the near old skeletal bone could be observed. The new bone formation is evaluated according to example 4 with confocal microscopy (samples washed in PBS are fixed in 4% formaldehyde/PBS solution with 0.2% Triton X100 for 30 min to 4° C.). The sample is washed twice in 0.1% BSA in PBS at room temperature for 10 min. Cells samples were analyzed with phaloidin-FITC and blue Hoechst for nuclear coloration and then incubated for 1 h to +4°.

Example 6

Formation and Development of the Woven LAB on Titanium Implants

Similarly to what is shown in example 5, LAB can, for example, colonize non reabsorbable surfaces like titanium dental implants or femoral prostheses. Using the same protocol for the example 5, prosthetic material surface is covered by cells within 7 days: osteointegration between biomaterials and the human woven bone occurs in vitro, limiting healing period, complications and failure risks. The effectiveness of the bone formation process is evaluated like in example 5.

The invention claimed is:

1. A homogenous stem cell population able to differentiate, without addition of specific factors, into osteogenic progenitors that express RUNX 2, from which subsequently osteoblasts derive that express HLA 1, CD44, RUNX 2, CD54 and osteocalcin, said homogeneous stem cell population being able to produce bone in vitro, and wherein said homogenous stem cell population is obtained by isolation from either human pulp of deciduous teeth (MBP-SHED Mesenchymal Bone Producing cells derived from Stem cell from Human Exfoliated Deciduous teeth), or from permanent teeth or dental germs (MBP-DPSC Mesenchymal Bone Producing cells derived from Dental Pulp Stem Cells) and by FAC sorting using c-kit, STRO-1 and CD34 markers.

* * * * *